United States Patent [19]

Robinson et al.

[11] 4,373,089

[45] Feb. 8, 1983

[54] PHENANTHRENE BASED POLYIMIDE RESIN

[75] Inventors: Joseph G. Robinson, Winchcombe; David I. Barnes, Cheltenham, both of England

[73] Assignee: Coal Industry (Patents) Limited, London, England

[21] Appl. No.: 240,007

[22] Filed: Mar. 3, 1981

[30] Foreign Application Priority Data

Mar. 19, 1980 [GB] United Kingdom ............ 8009255

[51] Int. Cl.³ ............................................. C08G 73/10
[52] U.S. Cl. ................................. 528/353; 428/473.5; 525/472; 528/220; 528/229; 528/233; 528/247
[58] Field of Search ............... 528/220, 233, 247, 353, 528/229; 525/472; 428/473.5

[56] References Cited

U.S. PATENT DOCUMENTS 3,078,279 2/1963 McCraken et al. ............ 260/346.4
4,173,573 11/1979 Schulz et al. ................... 260/346.4

FOREIGN PATENT DOCUMENTS 633923 12/1949 United Kingdom .

Primary Examiner—Lester L. Lee
Attorney, Agent, or Firm—Stevens, Davis, Miller & Mosher

[57] ABSTRACT

A polyimide resin is made by converting a phanthrene to its 9, 10 diol derivative, reacting the derivative with formaldehyde to give a methylene bridged reaction product, oxidizing the reaction product to produce a polycarboxylated product, and reacting the polycarboxylated product with an aromatic diamine to form the polyimide resin. The invention also includes the resin, the reaction product and the polycarboxylated product.

The resin will be useful as a lamp capping cement, a high temperature insulator, in copper clad printed circuit boards, in glass or asbestos laminates for use as compressor blades.

8 Claims, 1 Drawing Figure

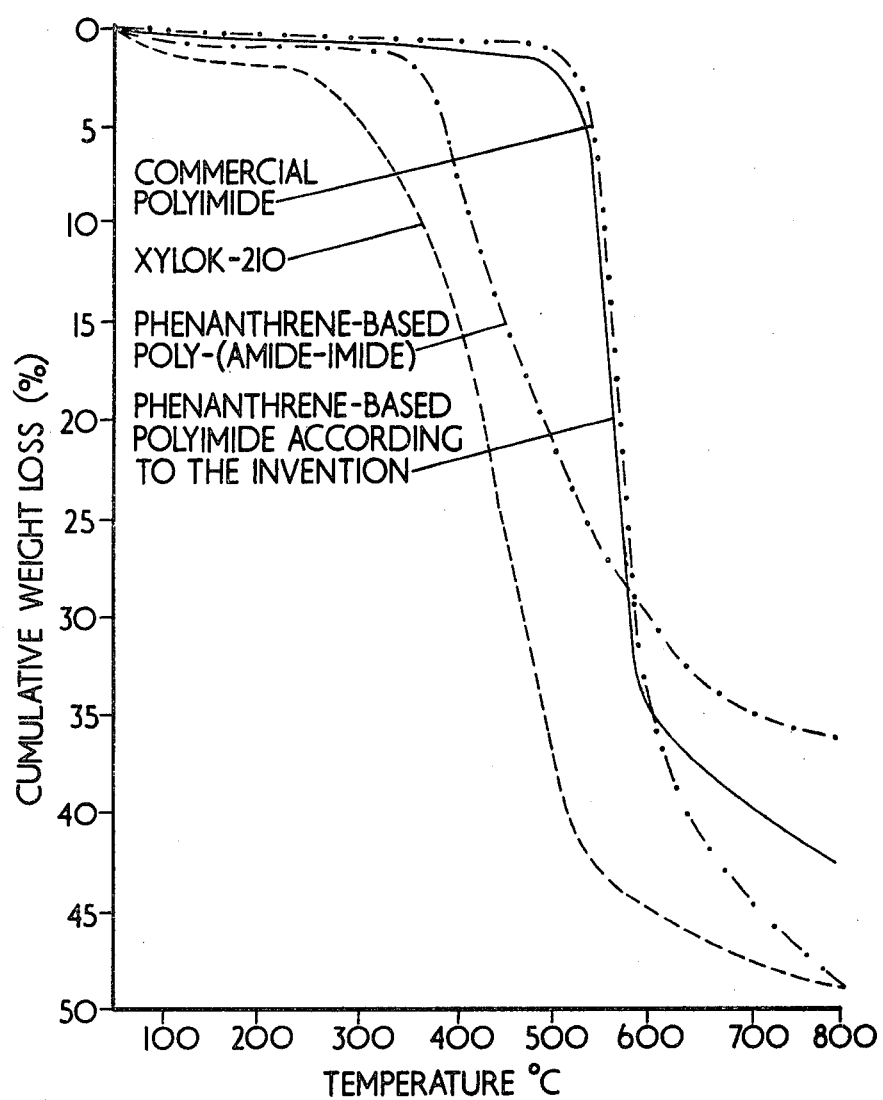

PHENANTHRENE BASED POLYIMIDE RESIN

This invention relates to a novel polyimide resin, a process for and intermediates in its preparation and its use as a thermally stable resin. In particular, but not exclusively, the invention relates to such a resin produced from cheaply available materials.

Several resins have been developed which are stable at high temperatures (in the region from 200° to 250° C. and even higher) and which retain their mechanical properties at these temperatures. These resins include polyimides, poly-(amide-imides), polybenzimidazoles, and polyphenylenes. These resins are derived from expensive materials and are difficult to make. They have limited commercial acceptability either because of their high cost or because their chemical or physical properties are not adequate for their intended use. There are also resins made by Friedel-Crafts-type reactions which are cheaper but less thermally stable than those mentioned above.

Another disadvantage of presently known resins is that they are made from petrochemicals. As the supply of petrochemicals is limited and rapidly decreasing, the cost of these resins will go up, and eventually it will not be possible to produce them economically. There is a need for a thermally stable resin which is relatively cheap, which is made from readily available materials and which has good mechanical and physical properties. Such a resin would find use as a lamp capping cement, as a high temperature insulator, in copper clad high temperature printed circuit boards, in electric heater panels, in transformers and in glass or asbestos laminates for use as compressor blades.

In our copending British patent application Nos. 79/32778 and 80/09254 we disclose two methods of producing poly-(amide-imide) resins from phenanthrene, involving the reaction of phenanthrene with formaldehyde in the presence of an acid catalyst. The resin produced contains both amide and imide linkages. The amide linkages are thought to be produced by the preferred reaction of formaldehyde at the 10-position of the phenanthrene nucleus. The mechanism by which this gives rise to amide linkages in the final resin is set out in our application No. 79/32778 mentioned above. The amide linkages are less thermally stable than are the imide linkages and so it is an aim of the present invention to provide a resin derived from phenanthrene containing substantially only imide linkages.

According to a first aspect of the present invention there is provided a method of producing a polyimide resin, comprising converting a phenanthrene to its 9, 10 diol derivative, reacting the derivative with formaldehyde or a formaldehyde donor in the presence of an acid catalyst to give a reaction product having substantially only methylene bridges between adjacent phenanthrene moieties, oxidising the reaction product to break the 9, 10 bond in the phenanthrene moieties to give a polycarboxylated product, which is dehydrated to its anhydride derivative and reacted with an aromatic diamine to form the resin.

The phenanthrene may be pure, or may be or contain one or more alkylated derivatives. Phenanthrene in a pure enough state may be readily obtained from the anthracene oil fraction of coal tar, which is produced during the carbonisation or liquid extraction of coal. These feedstocks will remain in plentiful supply for as long as coal stocks last.

Preferably the phenanthrene is converted to its 9, 10 diol derivative via the 9, 10 phenanthraquinone. The phenanthrene is oxidised by a mild oxidising agent, such as potassium dichromate, to produce the phenanthraquinone which is reduced to the 9, 10 phenanthrene diol by a mild reducing agent, such as sulphur dioxide. Sulphur dioxide is a convenient reducing agent because it is possible to bubble it through a solution of the phenanthraquinone to produce the 9, 10, diol derivative. The derivative can be protected from reoxidation by a blanket of an inert gas such as nitrogen.

Any other convenient route from the phenanthrene to its 9, 10 diol derivative may be used as long as suitable precautions are taken to prevent reoxidation of the derivative to the phenanthra-quinone.

The 9, 10 diol derivative reacts readily with formaldehyde in the presence of an acid catalyst because of the activating effect of the hydroxyl groups, which direct the formaldehyde to the 2 and 3 positions on the phenanthrene moieties. It may therefore be possible to use mild acids, such as oxalic acid, to catalyse the reaction.

The acid catalyst may be another protonic acid, such as hydrochloric acid or para-toluene sulphonic acid, or a Lewis acid, such as aluminium chloride, and is preferably sulphuric acid, advantageously having a concentration of 50% in water.

The formaldehyde may be supplied as formaldehyde itself, as formalin, (40% formaldehyde in water), or as paraform-aldehyde, a solid polymer of formaldehyde and water containing about 87% formaldehyde. To ensure that substantially only methylene bridges are obtained, it is preferred that the molar ratio of 9, 10-diol derivative to formaldehyde is about 1 to 1 and that 9, 10-diol derivative to acid catalyst is about 1 to 2. Preferably, the reaction of the 9, 10-diol derivative with formaldehyde is carried out in glacial acetic acid as the solvent. The glacial acetic does not dissolve the reaction product which therefore appears as an easily collectable precipitate.

Preferably, the reaction product is oxidised by use of a peroxy organic acid, such as peroxy-acetic acid. Conveniently, the oxidation is carried out in a non-ionic polar solvent such as dimethoxyethane, or dichloroethane. The oxidation reaction oxidises the 9, 10-bond to produce a dicarboxylic acid grouping, and also oxidises the methylene bridges to keto groups. The polycarboxylated product contains many adjacent carboxyl groups and most, if not all, of these are dehydrated to form anhydrides, for instance by treatment with acetic anhydride.

The anhydride derivative is reacted with an aromatic diamine, such as 1, 4-diamino benzene or 4, 4' diaminodiphenyl methane, and preferably, the anhydride derivative and the diamine are reacted in two stages. At room temperature a polyamic acid is formed, which is solvent soluble and can form a varnish. The polyimide is then formed by high temperature curing at about 300° C. Since it will not have been possible for any of the phenanthrene moieties to be joined at the 9 or 10 positions, because of the blocking effect of the hydroxyl groups, there will be substantially only diphenic acid analogues to react with the diamine, therefore giving substantially only imide bonds.

According to a second aspect of the present invention, there is provided a polyimide resin comprising the condensation product of a reaction between (1) an aromatic diamine and (2) a polycarboxylated product formed by reacting the 9, 10-diol derivative of a phenanthrene with formaldehyde and oxidising the reaction product to produce keto groups bridging the diphenic acid moieties produced.

According to a third aspect of the present invention, there are provided intermediates in the formation of a polyimide resin comprising firstly the reaction product of a 9, 10-diol derivative of a phenanthrene with formaldehyde in the presence of an acid catalyst, and secondly the reaction product which has been oxidised to produce keto groups bridging the diphenic acid moieties produced.

The polyimide resin will find use in any of the fields previously mentioned in this specification. The present invention also includes polyimide resin when made according to the first aspect of the invention, and varnishes including polyimide resins according to the invention.

The invention will now be described by way of example only, with reference to the accompanying drawing, which shows a graph of weight loss as a function of temperature for various resins as determined by thermogravimetric analysis. These data, therefore, show the thermal stability of the resins.

A polyimide resin was prepared as follows:

Phenanthrene (17.8 g), potassium dichromate (35 g in 50 g of water) and 98% sulphuric acid (100 g) were heated together at 60° C. for 4 hours, whereupon an excess of water was added to the mixture to cause the precipitation of crude 9, 10-phenanthraquinone. The quinone was purified as its bisulphite addition compound from which the pure product, having a melting point of 209°–211° C., was liberated on acidification with dilute hydrochloric acid.

The quinone (5.2 g) was suspended in a mixture of glacial acetic acid (400 g) and distilled water (50 g) and heated at 60° C. for 30 minutes. Sulphur dioxide was then bubbled into the suspension to convert the quinone to 9, 10-phenanthrene diol by mild reduction. After 30 minutes the gas flow was stopped and residual sulphur dioxide was flushed out of the solution with oxygen-free nitrogen. The solution of the diol derivative was kept under nitrogen in order to prevent any reoxidation of it by atmospheric oxygen.

98% sulphuric acid (100 g) was added incrementally to the diol derivative solution over a period of 1 hour. Thereafter formalin (19.7 g) was added and the mixture was held at 60° C. for 2 hours. At the end of the time an orange-brown reaction product precipitated from solution. The reaction mixture was diluted with an excess (1500 g) of water and the precipitate was filtered off.

The reaction product was analysed by gel permeation chromatography which demonstrated that 67% of it had a molecular weight from 1000 to 1500 and contained about 2% free 9, 10 phenanthrene diol. This impurity was removed by washing with boiling water under a nitrogen atmosphere.

The 9, 10 phenanthrene diol formaldehyde reaction product (10 g) was dissolved in 1,2 dichloroethane (400 ml), the temperature of the solution was raised to 80° C. and 40% peracetic acid in glacial acetic acid (350 g) was added over a period of 2 hours. The temperature was adjusted to maintain a slight reflux throughout the reaction period. The reaction product was oxidised to produce a polycarboxylated product which was isolated by adding the reaction mixture to water (2000 ml). The organic phase was separated out, filtered and the 1,2, dichloroethane distilled off to yield the crude polycarboxylated product. This was purified by dissolving it in 20% sodium carbonate solution and reprecipitating by the addition of an excess of 0.1 M hydrochloric acid. This was washed free of hydrochloric acid and dried in a vacuum desiccator. The polycarboxylated product was assumed to contain diphenic acid moieties linked by keto groups derived from the methylene bridges formed by the formaldehyde.

The polycarboxylated product (10 g) was converted to its anhydride by heating it with an excess (100 g) of acetic anhydride. The solution was cooled, diluted with water and filtered to recover the anhydride of the polycarboxylated product. This was dried in a vacuum desiccator.

The anhydride (10 g) was dissolved in dry dimethyl sulphoxide (DMSO) and added to a solution of an equivalent amount of 4,4'-diaminodiphenylmethane in DMSO. The mixture was held at room temperature and stirred until the viscosity of the solution had reached at least 100 cP. The solution was then poured onto a glass plate and heated to 350° C. to produce a tough flexible polyimide film.

The polyimide thus formed was tested for thermal stability by thermogravimetric analysis. The figure, to which reference is now made, shows the cumulative weight loss (%) as the abscissa and temperature as the ordinate. There are shown four lines, comparing the thermal stability of a petrochemically derived polyimide based on pyromellitic anhydride, a commercial Friedel Crafts resin, Xylok-210, a phenanthrene based poly-(amide-imide) resin made according to our previous application, and the resin made according to the process described above.

It can be seen from the figure that the resin according to the present invention is at least as thermally stable as of the other resins. Moreover it has better physical properties than the phenanthrene-based poly-(amide-imide) resin and is derived from a less expensive feedstock than is the commercial polyimide. It is envisaged that the resin will find use in those applications previously mentioned.

We claim:

1. A method of producing a polyimide resin comprising reacting a phenanthrene anhydride prepared by (1) converting a phenanthrene to its 9, 10 diol derivative; (2) reacting said derivative with formaldehyde or a formaldehyde donor in the presence of an acid catalyst to give a reaction product having substantially only methylene bridges between adjacent phenanthrene moieties; (3) oxidizing said reaction product to break the 9, 10 bond in the phenanthrene moieties to give a polycarboxylated product and (4) dehydrating said polycarboxylated product to produce its anhydride derivative; with an aromatic diamine to form the polyimide resin.

2. The method as claimed in claim 1, in which the phenanthene is converted in step (1) by mild oxidation to produce 9, 10 phenanthraquinone which is then reduced to its 9, 10 diol derivative.

3. The method as claimed in claim 1, in which step (2) is carried out using a mild acid catalyst and the molar ratios of the 9, 10 diol derivative to formaldehyde and to acid catalyst are about 1:1 and about 1:2 respectively.

4. The method as claimed in claim 1, in which the oxidation in step (3) is carried out using a peroxy organic acid.

5. The method as claimed in claim 1, in which the aromatic diamine is 1, 4-diamino benzene or 4,4' diaminodiphenyl methane.

6. The method as claimed in claim 1, wherein the reaction between the phenanthrene anhydride and the aromatic diamine is carried out in a first stage to form a polyamic acid followed by a second high temperature curing stage to form the polyimide.

7. The method as claimed in claim 1, wherein the reaction between the phenanthrene anhydride and the aromatic diamine is carried out in solution.

8. A polyimide resin produced by the method of claim 1.

* * * * *